US00PP23284P2

(12) United States Plant Patent
Laviana

(10) Patent No.: US PP23,284 P2
(45) Date of Patent: Dec. 25, 2012

(54) ***ECHINACEA* PLANT NAMED 'B'S KNEES'**

(50) Latin Name: ***Echinacea* hybrid**
Varietal Denomination: B's Knees

(75) Inventor: Marc Richard Laviana, Kensington, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 0 days.

(21) Appl. No.: 13/374,632

(22) Filed: Jan. 4, 2012

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of hybrid *Echinacea*, 'B's Knees', characterized by its leaves that are lanceolate in shape with a shiny leaf surface, its sturdy stems that reach about 60 cm in height, its inflorescences with ray florets that are dark pink in color, and its continuous bloom from June to August with rebloom if spent blossoms are removed.

2 Drawing Sheets

Botanical classification: *Echinacea* hybrid.
Variety denomination: 'B's Knees'.

BACKGROUND OF THE INVENTION

The present invention relates to a new and distinct cultivar of *Echinacea* of hybrid origin and will be referred to hereafter by its cultivar name, 'B's Knees'. 'B's Knees' represents a new purple coneflower, an herbaceous perennial grown for landscape use.

The new cultivar arose as from a controlled cross made by the Inventor in 2006 in Kensington, Conn. The cross was made between *Echinacea purpurea* 'Kim's Knee High' (U.S. Plant Pat. No. 12,242) as the female parent and *Echinacea* 'CBG Cone 2' as the male parent (U.S. Plant Pat. No. 18,546). 'B's Knees' was selected as a single unique plant from the above cross in 2008.

Asexual reproduction of the new cultivar was first accomplished by in vitro propagation in Rijswijk, The Netherlands in 2008 under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'B's Knees' as a unique cultivar of *Echinacea*.

1. 'B's Knees' exhibits leaves that are consistently lanceolate in shape (indicating hybrid origin) with a shiny leaf surface.
2. 'B's Knees' exhibits large composite flowers with ray florets that are dark pink in color.
3. 'B's Knees' exhibits sturdy stems that reach about 60 cm in height.
4. 'B's Knees' blooms continuously from June to August and reblooms if spent blossoms are removed.

The new cultivar can be most closely compared to its parent plants, 'Kim's Knee High' and *Echinacea* 'CBG Cone 2'.

'B's Knees' is similar to 'Kim's Knee High' in floriferous blooming habit, however 'B's Knees' differs from 'Kim's Knee High' in having more lanceolate shaped foliage, sturdier flower stems, darker green foliage, and in having inflorescence ray florets that are darker pink in color. 'B's Knees' is similar to 'CBG Cone 2' in its floriferous blooming habit, however 'B's Knees' differs from 'CBG Cone 2' in having foliage that is less pubescent and shinier, in having taller and more sturdy flowering stems, and in having inflorescence ray florets that are darker pink in color. 'B's Knees' also can be compared to the cultivar Red Knee High (U.S. Plant Pat. No. 20,411). 'Red Knee High' differs from 'B's Knees' in having ray florets that are lighter pink in color.

BRIEF DESCRIPTION OF THE DRAWING

The plants in the accompanying photographs depict the characteristics of one year-old plants of 'B's Knees' as grown in one-gallon containers in Kensington, Conn.

The photograph in FIG. 1 shows a close-up of an inflorescence.

Figure 1:
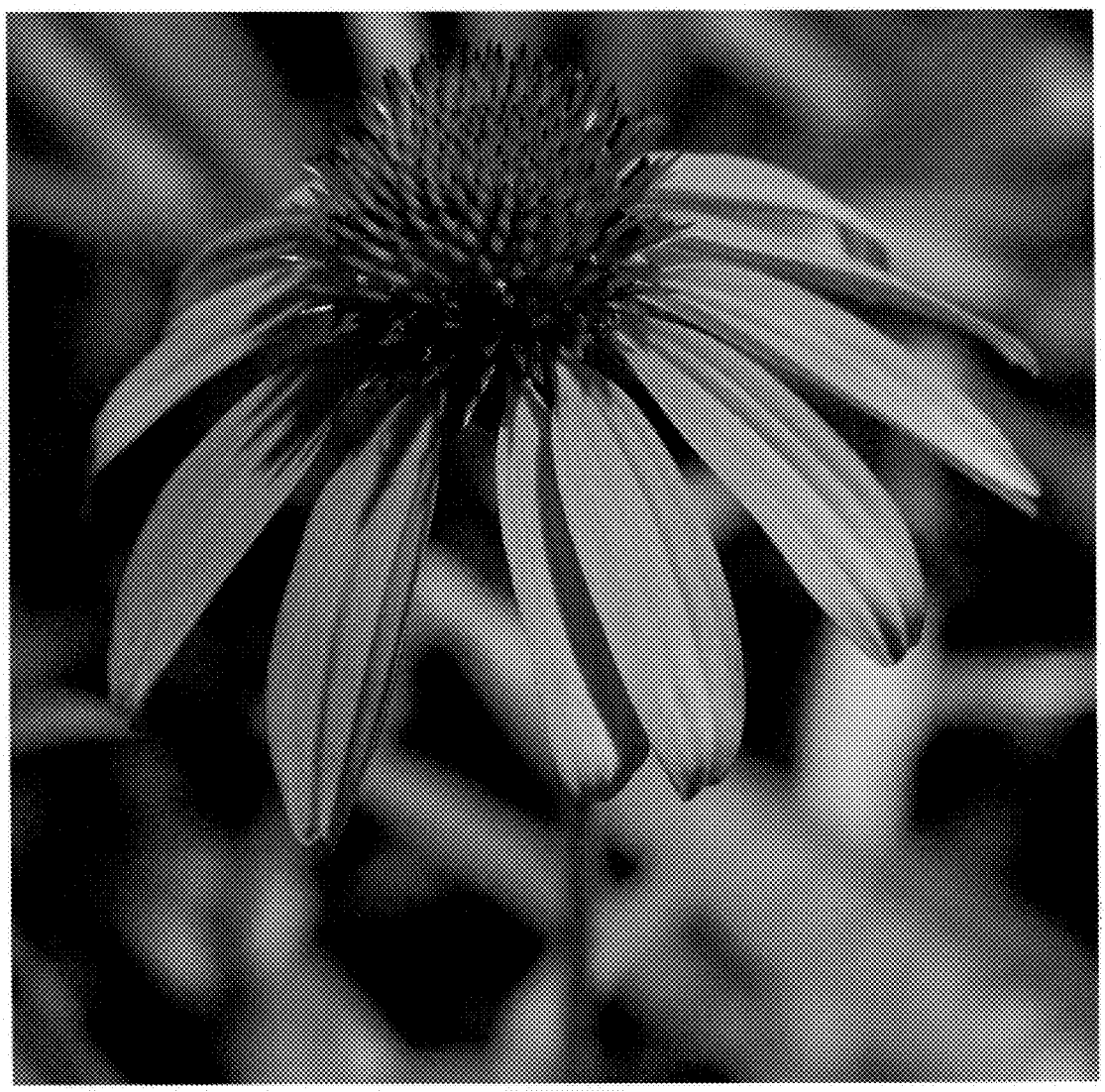
Figure 2:
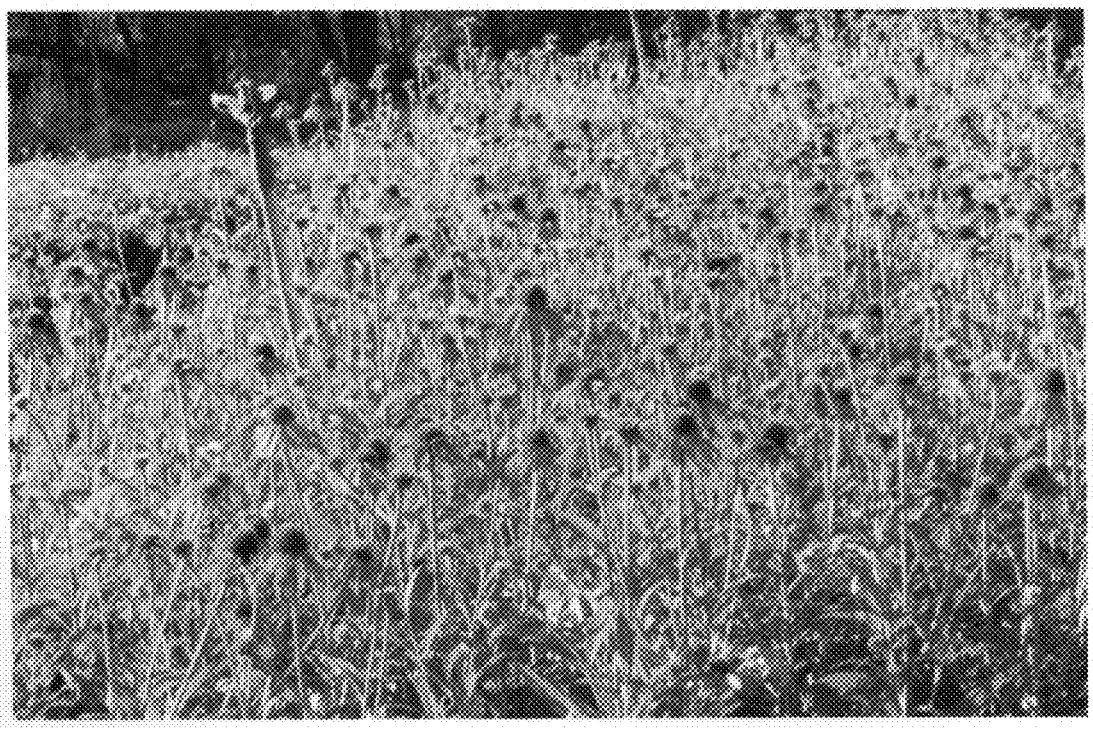

The photograph in FIG. 2 depicts a block of plants and shows the tall sturdy flowering stems.

Figure 3:
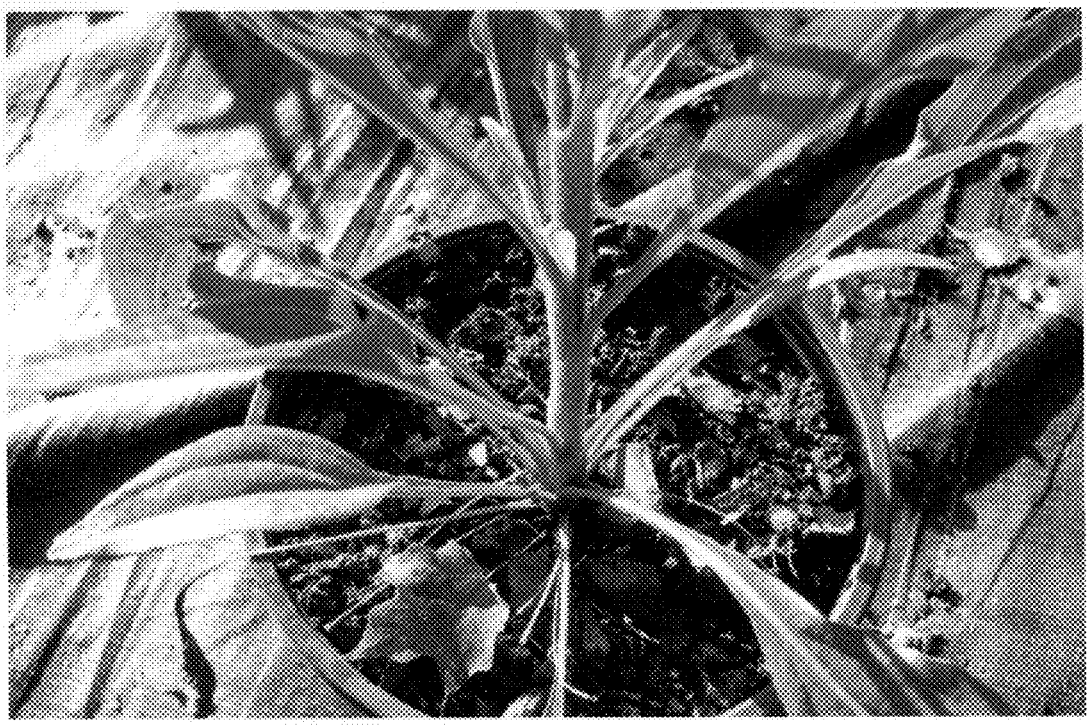

The photograph in FIG. 3 provides a close-up view of a flowering stem.

The colors in the photograph may differ slightly from the color values cited in the detailed botanical description, which accurately describe the colors of the new *Echinacea*.

BOTANICAL DESCRIPTION OF THE PLANT

The following is a detailed description of a one-year-old plant of the new cultivar as grown in a garden in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Continuously from June to August with rebloom if spent blooms are removed.

*Plant habit*.—Herbaceous perennial, clump-forming, upright, loosely but freely branched.

*Height and spread*.—About 60 cm in height and 60 cm in spread when mature (50 cm in height and 30 cm in height on a one year-old plant).

*Cold hardiness*.—At least to U.S.D.A. Zones 5.

*Diseases and pests*.—Resistance to powdery mildew has been observed under the conditions tested.

*Root description*.—Fibrous.

Growth and propagation:

*Propagation*.—Tissue culture preferred.

*Growth rate*.—Vigorous.

Stem description:

*Shape*.—Slightly oval, solid.

*Stem color*.—144A with vertical markings of 166A.

*Stem size*.—Average of 3 mm in diameter and an average of 30 cm in height including peduncle (one year-old plant), reaching up to 55 cm on a mature plant.

*Stem surface*.—Moderately covered with short stiff white hairs about 1 mm in length.

*Stem number*.—An average of 4 on a one year-old plant.

*Branching*.—4 to 5 branches per stem.

Foliage description:

*Leaf shape*.—Lanceolate.

*Leaf division*.—Simple.

*Leaf base*.—Cuneate to leaf-like petiole.

*Leaf apex*.—Acuminate.

*Leaf venation*.—Tri-nerved, upper surface; 145B to 145C in color with mid rib prominent towards base, lower surface; only mid rib is conspicuous, 138B in color on apical portion and 145A in color towards base.

*Leaf margins*.—Entire and minutely ciliate.

*Leaf attachment*.—Petiolate.

*Leaf arrangement*.—Alternate.

*Internode length*.—An average of 4.5 cm.

*Leaf size*.—Matures to an average of 10 cm in length and 2 cm in width.

*Leaf color*.—Newly formed upper surface; a blend of 138C and 144A, newly formed lower surface; 138A with pubescence of 138C, mature upper surface; a blend of 137A, 137B, and 137C, mature lower surface; 137B with pubescence of 138C.

*Leaf surface*.—Upper surface is shiny and very finely puberulent, lower surface is very finely puberulent but glaucous in appearance.

*Petioles*.—Leafy and extended from leaf blade, an average of 2.5 cm in length, typically about 6 mm in width at leaf blade and about 4 mm in width at stem, curved slightly inward on upper surface, same color as leaf on leafy edges and center portion is 145B on upper surface and 145C on lower surface.

Flower description:

*Type*.—Capitulum, heterogamous with ray florets around the head margin and disk florets in the center, forming a radiant head.

*Capitulum number*.—One terminal capitulum per branch, 4 to 5 per stem.

*Lastingness of inflorescence*.—About 10 days until senescence of ray flowers, disk flowers are persistent.

*Capitulum size*.—Matures to about 4.5 cm in depth and 8 cm in diameter, disk size is about 2 cm in depth and 3 cm in diameter.

*Fragrance*.—None.

*Involucral bracts or phyllary*.—About 44 arranged in 3 overlapping rows, up to 8 mm in length and 2.5 mm in width, fused at base, narrowly acute apex, lanceolate in shape, color on upper and lower surface a blend of 137C to 137D with mid rib 145C, entire ciliate margin and glabrous on both surfaces.

*Buds*.—Cup-shaped, up to 2.5 cm in diameter and 2.5 cm in height, phyllary is 137B in color with mid ribs 145C in color, ray florets are 145C in color, disk florets are 145C in color.

*Peduncle*.—Strong, continuous with stem, up to 17 cm in length and an average of 3.8 mm in diameter widening to about 6 mm at base of capitulum, 144A in color with vertical markings of 166A, texture is rough with short stiff white hairs.

*Ray florets* (*sterile*).—About 13, oblong-elliptic in shape, vertical ridges on both surfaces, about 3.5 cm in length and 1 cm in width, emarginated apex, cuneate base, entire margin except apex, upper and lower surface is glabrous with a slight sheen on lower surface, initially held upright about 45° from horizontal and become horizontal, then slightly reflexed as they mature, color of upper and lower surface when just before opening (when curled into tube); 160C, with lower surface becoming 160C in center with edges suffused with 63C and upper surface a blend of 63B and 63C, color of upper surface when fully open; 60C, color of lower surface when mature; blend of 63A and 68B with very tips 160B.

*Disk florets* (*bisexual*).—Numerous, about 160, tubular in shape, about 1 cm in length and 2 mm in width, arranged spirally on a receptacle, surrounded by a palea; 1.3 cm in length and 1.5 mm in width, lanceolate in shape with an apex that terminates in a spine, color is 145A with an a spiny apex 34B blending into 21A towards base, lobed petals (5) are fused into tube about 8 mm in length and 2 mm in width and 145C in color with apex 183A.

*Receptacle*.—Globose in shape, about 8 mm in diameter and height, color 195B.

Reproductive organs (present on disk florets only):

*Gynoecium*.—Pistil; 1, 7 mm in length and 3 mm in width (stigma portion), style; 0.3 mm in width and 5 mm in length, 145D in color, surrounded by stamens, stigma; bifid, each arm is reflexed, about 1.5 mm in length and 3 mm in width and 185A in color with tips 187A, ovary; inferior, single-celled, 3 mm in length and 2 mm in diameter, 145D in color.

*Androcoecium*.—Stamens; 5, fused, form a cylinder around style, 4 mm in length and 0.7 mm in width, dehisced longitudinally, 200A in color filaments; 0.7 mm in length, 0.3 mm in width, 1D in color, pollen; low in quantity and 17B in color.

*Fruit*.—An achene, 5 mm in length and 0.8 mm in width, 200B in color.

It is claimed:

1. A new and distinct cultivar of *Echinacea* plant named 'B's Knees' substantially as herein illustrated and described.

* * * * *